(12) United States Patent
Levi et al.

(10) Patent No.: US 7,549,421 B2
(45) Date of Patent: Jun. 23, 2009

(54) METHOD AND SYSTEM FOR INTEGRATING VENTILATOR AND MEDICAL DEVICE ACTIVITIES

(75) Inventors: Andrew P. Levi, Madison, WI (US); Andrea Tzanetakis, Madison, WI (US)

(73) Assignee: Datex-Ohmeda Inc., Madison, WI (US)

( * ) Notice: Subject to any disclaimer, the term of this patent is extended or adjusted under 35 U.S.C. 154(b) by 612 days.

(21) Appl. No.: 10/939,534

(22) Filed: Sep. 13, 2004

(65) Prior Publication Data

US 2005/0056283 A1 Mar. 17, 2005

Related U.S. Application Data

(60) Provisional application No. 60/503,604, filed on Sep. 17, 2003.

(51) Int. Cl.
*A61M 11/00* (2006.01)

(52) U.S. Cl. .............................. 128/204.21; 128/204.18

(58) Field of Classification Search ................................
128/204.21–204.23, 203.12, 204.18, 204.13,
128/203.25
See application file for complete search history.

(56) References Cited

U.S. PATENT DOCUMENTS

| | | | | |
|---|---|---|---|---|
| 4,387,722 A | | 6/1983 | Kearns | |
| 4,471,773 A | * | 9/1984 | Bunnell et al. | 128/204.21 |
| 4,747,403 A | * | 5/1988 | Gluck et al. | 128/204.21 |
| 5,957,129 A | * | 9/1999 | Tham et al. | 128/204.28 |
| 6,074,345 A | * | 6/2000 | van Oostrom et al. | 600/300 |
| 6,105,575 A | | 8/2000 | Estes et al. | |
| 6,216,690 B1 | * | 4/2001 | Keitel et al. | 128/203.12 |
| 6,467,477 B1 | | 10/2002 | Frank et al. | |
| 6,584,973 B1 | * | 7/2003 | Biondi et al. | 128/204.21 |
| 6,718,975 B2 | * | 4/2004 | Blomberg | 128/204.23 |
| 6,820,618 B2 | * | 11/2004 | Banner et al. | 128/204.23 |
| 2003/0070681 A1 | | 4/2003 | Rydgren | |

FOREIGN PATENT DOCUMENTS

| | | |
|---|---|---|
| EP | 1 308 178 | 5/2003 |
| WO | 99/43254 | 9/1999 |

* cited by examiner

*Primary Examiner*—Steven O Douglas
(74) *Attorney, Agent, or Firm*—Andrus, Sceales, Starke & Sawall, LLP

(57) ABSTRACT

A method for integrating a ventilator device with a monitoring device and other medical devices that allows the function of the monitoring device and medical devices to automatically change based on initiation of a respiratory therapy procedure. In addition, modification of behavior on the part of the ventilator is automatic in response to activation of a medical procedure from the medical device or the monitoring device.

38 Claims, 4 Drawing Sheets

METHOD AND SYSTEM FOR INTEGRATING VENTILATOR AND MEDICAL DEVICE ACTIVITIES

CROSS-REFERENCE TO RELATED APPLICATION

The present application is based on and claims priority to U.S. Provisional Patent Application Ser. No. 60/503,604, filed Sep. 17, 2003.

FIELD OF THE INVENTION

The present invention relates to a method of providing respiratory therapy to a patient. More particularly, the invention relates to a method of integrating the active behaviors of a ventilator and a medical device or a monitoring device to provide improved respiratory therapy or monitoring behaviors.

BACKGROUND OF THE INVENTION

Contemporary ventilators often provide for the use of ventilation "procedures", which may require a transient change in ventilator operation. Examples of such ventilation procedures include pre-oxygenating a patient for several minutes prior to suctioning the airway, transiently occluding the patient circuit at the end of an exhalation, changing the $O_2$ delivery percentage for the purpose of Functional Residual Capacity measurement, etc.

Associated with these ventilation procedures, it is often desirable to modify the behavior of the monitoring device, either to initiate a measurement or to protect the monitoring device from damage. Conversely, it is also often desirable to initiate certain ventilation procedures in association with an attempt to take a reading of a specific monitoring parameter.

Historically, ventilators and monitoring devices have typically been separate units having their own displays and user interfaces. However, by the present invention it is recognized as desirable to integrate the ventilator and monitoring device functions to operate as a single respiratory care system. By this innovative system approach, monitoring data from the monitoring device is displayed together with ventilation therapy information on a single configurable display. Although some examples of this concept are shown in the prior art, as for example critical care monitoring devices that can receive and display certain ventilation therapy information via serial communication attachments, the prior art devices do not fully integrate the active behaviors of the ventilator and the monitoring device. In other words, while prior art monitoring and ventilation devices have been integrated in terms of the data that is moved between them, they are not integrated as to their active behaviors so as to achieve desired clinical performance.

The prior art ventilation and monitoring devices thus require individual adjustments by the user to effect a desired therapy or simple physiologic measurement behavior. This can require time consuming and tedious manual operations and therefore undesirably reduces system efficiency.

Like the relationship that exists between ventilation and monitoring devices, a similar inter-relationship exists between currently available ventilators and various other medical devices. For example, imaging devices such as MRI, CAT scans and radiograms, as well as drug delivery devices such as nebulizers and syringe pumps, are utilized in the same operating environment as the prior art ventilation devices. In some cases, when the medical device is operated to perform a medical procedure, the operation of the ventilator must be modified in order to provide the optimal conditions for the performance of the medical procedure. For example, at the start of a lung radiogram, it is desirable for the ventilator to inflate the lungs to a specific pressure level. In currently available systems, the ventilator must be manually operated independently from the operation of the radiogram to obtain the desired lung pressure.

It is therefore desirable to provide a method that integrates the active behaviors of a ventilator and either a monitoring device and/or other medical device so as to efficiently and automatically achieve a single desired clinical performance. More specifically, it is desirable to provide a method whereby a monitoring device, a medical device and a ventilator provide appropriate inputs into the control of each other's behavior. It is desirable to achieve this integrated behavior automatically, thereby reducing the amount of tedious, non-value added tasks to be conducted by a clinician. Further, it is desirable to achieve this behavior automatically such that the desired actions are performed accurately to provide proper integrity to the acquired monitored data. It is also desirable to perform these actions automatically so as to maximize protection of the equipment being utilized.

SUMMARY OF THE INVENTION

By the present invention, a method of integrating the active behaviors of a ventilator and either a monitoring device or other medical device is provided. More specifically, the invention relates to a method whereby a ventilator is integrated with a respiratory gas monitoring or other monitoring device and the function of the monitoring device is changed based on initiation of a respiratory therapy procedure by the ventilator. The invention also relates to modification of behavior on the part of the ventilator in response to activation of a medical procedure from a medical device, an imaging device, a monitoring device or a drug delivery device.

In one embodiment, the method of integrating the active behaviors of the ventilator and the gas monitoring device comprises the steps of (1) detecting the activation of a respiratory therapy procedure, and (2) automatically modifying the operating condition of the respiratory gas monitoring device in conjunction with the modification to the ventilator operation upon the beginning of the respiratory therapy procedure. Once the settings of the respiratory gas monitoring device have been modified, the method may include the step of further modifying the operating condition of the respiratory gas monitoring device based upon detection of the cessation of the respiratory therapy procedure. Alternately, the setting of the respiratory gas monitoring device may be further modified after a predetermined time period. If desired, the setting of the respiratory gas monitoring device can be automatically returned to the operation condition as existed prior to the activation of the respiratory therapy procedure.

In another embodiment, the method comprises the step of modifying the behavior of the ventilator in response to activation of a transient parameter measurement from the respiratory gas monitoring device. More specifically, as a transient parameter measurement from the respiratory gas monitoring device is initiated, the method comprises the step of modifying the behavior of the ventilator in response to this initiation of the transient parameter measurement.

In addition to utilizing the method with the integration of a ventilator and a respiratory gas monitoring device, the method also contemplates the integration of the active behaviors of the ventilator and some other type of medical device. As an example, the active behaviors of the ventilator can be integrated with medical devices such as imaging devices and drug delivery devices. The steps of integrating the active behaviors of the medical device and the ventilator include providing a control unit in communication with both the ventilator and the medical device. The control unit is configured to detect the beginning of a respiratory therapy procedure initiated at the ventilator. Upon the detection of the beginning of the respiratory therapy procedure, the ventilator begins its ventilation procedure and the control unit generates a modification signal that automatically modifies the operating condition of the medical device to optimize the conduct of the overall respiratory therapy procedure being provided. The operating condition of the medical device is modified by initiating a modification signal within the control unit of the ventilator and providing the modification signal to the medical device. Upon receiving the modification signal, the medical device conforms its operating conditions to an optimal condition based on the respiratory therapy procedure. In this manner, the operation of the medical device and the operation of the ventilator are coordinated automatically to optimize the operating conditions of both devices.

In yet another alternate embodiment, the operating conditions of the ventilator are modified based upon the detection of the beginning of a medical procedure. Upon the activation of a medical procedure at the medical device, the operation of the ventilator is adjusted to optimize the performance of the medical device in executing the medical procedure. This modification is automatically completed without the requirement of additional clinician control.

Preferably, the method of the present invention is carried out by an apparatus that includes a control unit in the ventilator. The control unit within the ventilator is in communication with various other remote monitoring devices and medical devices. During normal operation, the ventilator is capable of performing various ventilation procedures, while the monitoring device can perform various monitoring procedures and the medical device can perform various medical procedures. The control unit is operable to coordinate a respiratory therapy procedure in which a combination of the ventilation, monitoring and medical procedures is automatically coordinated to optimize the respiratory therapy procedure.

Upon receiving an indication of either a monitoring procedure, a medical procedure, or the beginning of a therapy procedure, the control unit is capable of modifying the operating conditions of any of the ventilator, monitoring device or medical device to optimize the procedure being executed. The single, central control unit allows the functions of the multiple devices to be integrated and coordinated.

BRIEF DESCRIPTION OF THE DRAWINGS

The drawings illustrate the method most presently contemplated of carrying out the invention.

In the drawings.

DETAILED DESCRIPTION OF THE PREFERRED EMBODIMENT

In the preferred embodiment of the present invention described in detail below, a method of integrating the active behaviors of a ventilator and either a monitoring device or a medical device, or both, is provided. It should be understood that the drawings and specification are to be considered an exemplification of the principles of the invention, which is more particularly defined in the appended claims. For example, although the basic steps of the method of the invention are applied for use with specific respiratory therapy procedures, such as the nebulization of a therapeutic drug or a cardiac wedge pressure measurement, it is contemplated that the present method is applicable to a variety of known respiratory therapy procedures beyond those specifically described below. In general, a respiratory therapy procedure is a combined procedure carried out by the ventilator control unit and two or more of a ventilator, a monitoring device, drug delivery device, imaging device or other medical device. During normal operation, the ventilator is capable of performing ventilation procedures, while the medical device can perform multiple medical procedures and the monitoring device can perform multiple monitoring procedures. The present invention integrates the transient changes in the procedures of these devices during a respiratory therapy procedure to optimize the performance of the respiratory therapy procedure through the use of a control unit preferably contained in the ventilator.

An exemplary embodiment of the present invention relates to a method wherein a ventilator is integrated with a respiratory gas monitoring device and the function of the respiratory gas monitoring device is changed based on initiation of a respiratory therapy procedure. Although the above example contemplates the use of a gas monitoring device, various other types of monitoring devices can be utilized with the present invention. Throughout the following description, the term monitoring device will describe a broad class of devices, while the term respiratory gas monitoring device will describe a specific type of monitoring device.

Figure 1:
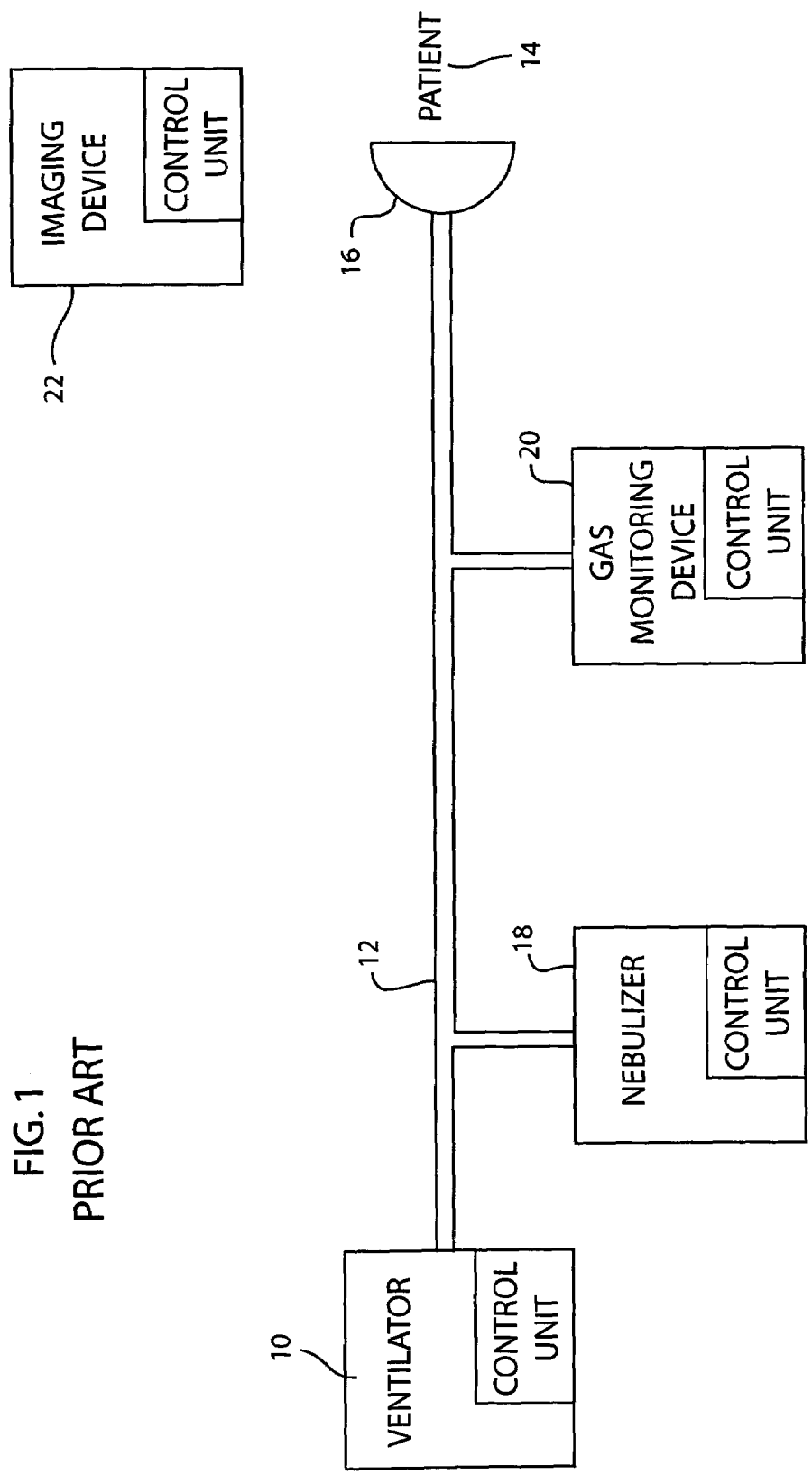
FIG. 1 is a schematic illustration of a prior art configuration for a ventilator, drug delivery device, gas measurement device and medical device.

Referring first to FIG. 1, thereshown is a typical, prior art configuration of a ventilation system for providing a flow of ventilation gas to a patient. As illustrated, a ventilator 10 provides a flow of ventilation gas through a patient conduit 12 to the patient 14. In the embodiment illustrated in FIG. 1, the patient receives the flow of ventilation gas through a gas mask 16, although various other types of delivery connections are contemplated as being within the scope of the present invention.

As illustrated in FIG. 1, the patient conduit 12 can receive a dose of medication from a nebulizer 18. Additionally, the patient conduit 12 can be coupled to a respiratory gas monitoring device 20 that operates to monitor the contents and quality of the ventilator flow to the patient 14. The system shown in FIG. 1 may also include an imaging device 22 that can be separately operated to take desired images of the patient during the use of the ventilator 10.

As described above, the ventilator and other associated devices can be operated to carry out various different respiratory therapy procedures. An example of a respiratory therapy procedure is the application of nebulized medicine to a breathing circuit during ventilation therapy. To medicate a patient on a ventilator, a drug delivery device, such as the nebulizer 18, introduces aerosolized medication periodically as prescribed into the breathable gas flowing through the inspiratory patient conduit 12 of the patient circuit and ultimately to the patient's airway and lungs. Because the medicine typically used in respiratory care, such as Albutoral, is very sticky, the materials can cause damage to components such as pumps and infrared benches found in respiratory gas monitoring devices 20. Thus, it is desirable to suspend the operation of the respiratory gas monitor pump during the period of the nebulization procedure and perhaps for a brief time afterward in order to allow the medicine to clear the breathing circuit.

As can be understood in FIG. 1, since the ventilator 10, nebulizer 18 and respiratory gas monitoring device 20 do not communicate with each other, during the operation of the nebulizer 18 the operation of the gas monitoring device 20 must be manually suspended while the nebulizer 18 introduces the aerosolized medication into the patient conduit 12. Once the desired amount of nebulized drug has been delivered, (sometimes 10-30 minutes later), the user needs to remember to return into the patient's room to reinitiate the gas monitoring device 20. In many cases, the nebulizer delivers drugs several times a day, which can become a tiresome and time-consuming proposition for the user.

Figure 2:
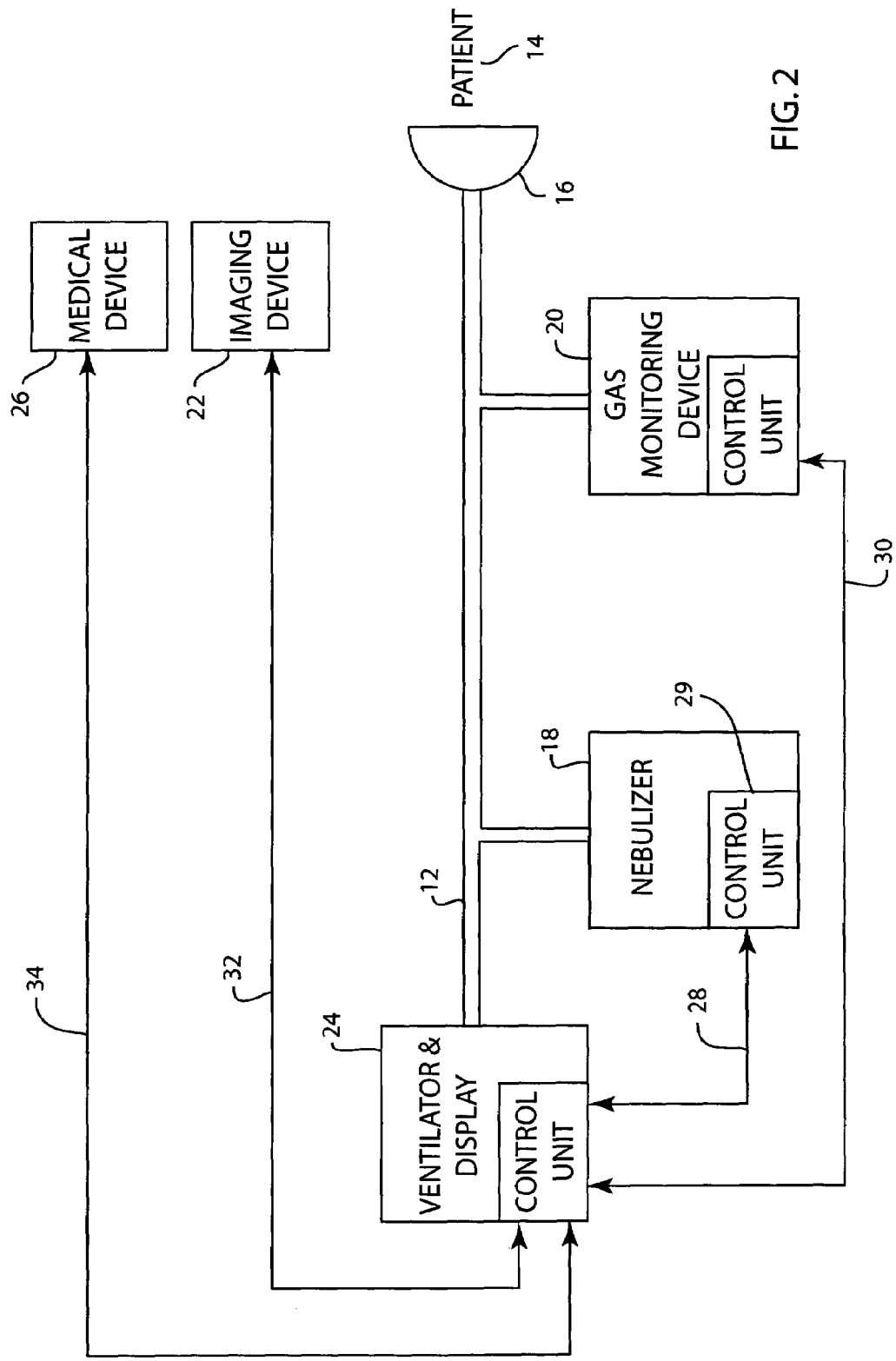
FIG. 2 is a graphic illustration of the integration of the ventilator, drug delivery device, gas measurement device and medical devices in accordance with the present invention.

Referring now to FIG. 2, thereshown is a preferred configuration for the method and system of the present invention. As illustrated in FIG. 2, the ventilator and integrated display 24 provide a ventilation gas flow through the patient conduit 12 to the patient 14. Likewise, the nebulizer 18 and a monitoring device, such as a respiratory gas monitoring device 20 are each in communication with the patient conduit 12. Thus, the nebulizer 18 is able to introduce an aerosolized medication into the flow of gas within the patient conduit 12, while the gas monitoring device 20 is able to make the desired measurements of the ventilator gas flow as desired.

As illustrated, the system includes an imaging device 22, in addition to various other medical devices 26. In the embodiment of the invention illustrated in FIG. 2, the control unit 27 of ventilator and display 24 is in communication with a control unit 29 of the nebulizer 18 over a communication link 28. Likewise, the control unit of the ventilator and display 24 is in communication with the respiratory gas monitoring device 20 over a second communication link 30. In this manner, the control unit 27 of the ventilator and display 24 can communicate in a bi-directional manner with both the nebulizer 18 and the respiratory gas monitoring device 20.

In addition, the control unit 27 of the ventilator and display 24 is also in 2-way communication with the imaging device 22 over a third communication link 32 and with the other medical devices 26 over additional communication links 34.

In the embodiment of the invention illustrated in FIG. 2, the communication link 28 between the ventilator 24 and the nebulizer 18 is an RS-422 connection. However, it is contemplated that all of the communication links 28, 30, 32 and 34 could be replaced by any method of communicating over a point to point network. As an example, electrical and RF communication methodologies are contemplated as being within the scope of the present invention.

In the embodiment of the invention illustrated in FIG. 2, the nebulizer 18, monitoring device 20, and imaging device 22 are separate components from the ventilator 24 such that each of the devices includes it own control unit. In such an embodiment, the control unit 27 from the ventilator 24 communicates in a bi-directional manner with the control unit 27 for the nebulizer 18. In the embodiment illustrated, the nebulizer 18, gas monitoring device 20 and imaging device 22 are located remotely from the ventilator 24 such that the communication link between the various devices is typically carried out by a RS-422 cable. However, it is contemplated that the control units for any or all of the nebulizer 18, gas monitoring device 20 and imaging device 22 could be integrated into a single cabinet or structure with the ventilator and display 24. In such an embodiment, the RS-422 communication links could be replaced by conventional wiring. It is also contemplated that some of the communication links between the control unit and the remote devices may be uni-directional. In the most basic embodiment of the remote devices, the control unit of the device may consist only of analog circuits necessary to activate the monitor or medical device. For example, the nebulizer 18 may include a control unit consisting of only analog electronic circuits necessary to power the nebulizer. The control signal to such a nebulizer would be the power control input for the analog circuits.

As can be understood in FIG. 2, the control unit 27 contained within the ventilator 24 is able to communicate with multiple different devices each used during the ventilation and monitoring of a patient 14. The ventilator 24 is able to communicate with and provide control signals to the nebulizer 18, gas monitoring device 20, imaging device 22, and various other medical devices 26. In this manner, the single control unit 27 of the ventilator 24 is able to trigger and provide control signals to the various components based upon the ventilation therapy procedures being carried out by the ventilator 24.

Figure 3:
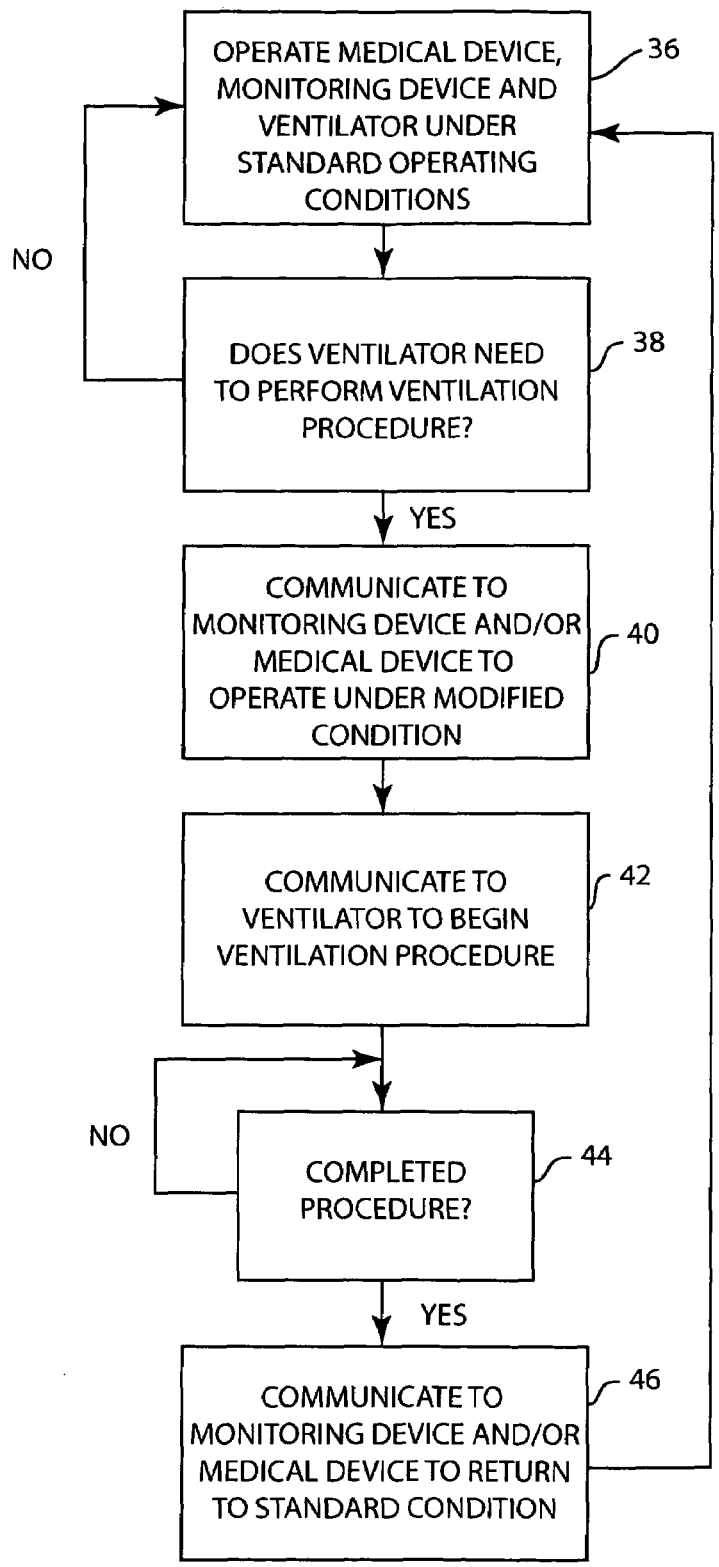
FIG. 3 is a schematic depiction of the steps of a method where the function of a monitoring device or medical device is changed based upon the initiation of a respiratory therapy procedure.

Referring now to FIG. 3, in accordance with a first embodiment of the present method, the medical device, monitoring device and ventilator are all initially operated under standard operating conditions, as shown in step 36. During the normal course of operation, the control unit contained within the ventilator monitors the operation of the medical device, the monitoring device and the ventilator to determine whether any procedures are to be performed by any of these components. In step 38, the control unit of the ventilator determines whether the ventilator has initiated a respiratory therapy procedure, either automatically or by a manual user input. If the ventilator has not initiated such a procedure, the control unit returns to the initial step 36 and continues to monitor for the initiation of a respiratory therapy procedure.

If the control unit of the ventilator detects the initiation of a respiratory therapy procedure, the control unit sends a signal to the ventilator, monitoring device and the medical device to operate under modified operating conditions, if modified conditions are required to optimize the respiratory therapy procedure.

As an example, the ventilator can be configured to perform a periodic sigh (greater than normal inspiration) and such procedure should not interfere with the gas monitoring trend sample function. In such situations, the control unit of the ventilator sends a modification signal to the control unit of the monitoring device, causing the monitoring device to suspend trend operation during the periodic sigh. Additionally, if medical devices are coupled to the ventilator and may be affected by the periodic sigh, the ventilator control unit provides the required signal to the medical device, causing the medical device to operate under modified conditions.

Once the modification signals have been sent to the monitoring device and the medical device, the control unit signals to the ventilator to begin its ventilation procedure in step 42. The combination of these events comprises the respiratory therapy procedure being coordinated by the control unit.

After the ventilator has completed its ventilation procedure in step 44, the control unit communicates to the monitoring device and medical device to return to the standard operating conditions, as indicated in step 46. As the above description indicates, during the respiratory therapy procedure the control unit coordinates the operation of not only the ventilator operating parameters, but also the operation of related medical devices and monitoring devices utilized throughout the system.

The invention thus solves the drawbacks of the prior art by automatically modifying the behavior of the monitoring device in response to the activation (or inactivation) of the respiratory therapy procedure, increasing efficiency and accuracy of the respiratory therapy procedure.

It is recognized that the above-described method is useful for a wide variety of respiratory therapy applications, including the performance of certain monitoring calibrations (e.g. a 100% oxygen span calibration on the monitoring device in association with a pre-oxygenation maneuver) and the initiation of monitoring data samples at appropriate times in a procedure cycle (e.g. sampling respiratory gases at specific points in a procedure). During the respiratory therapy procedures, the control unit integrates the transient changes in operation of the ventilator, monitoring device or other medical device to optimize the procedure.

Figure 4:
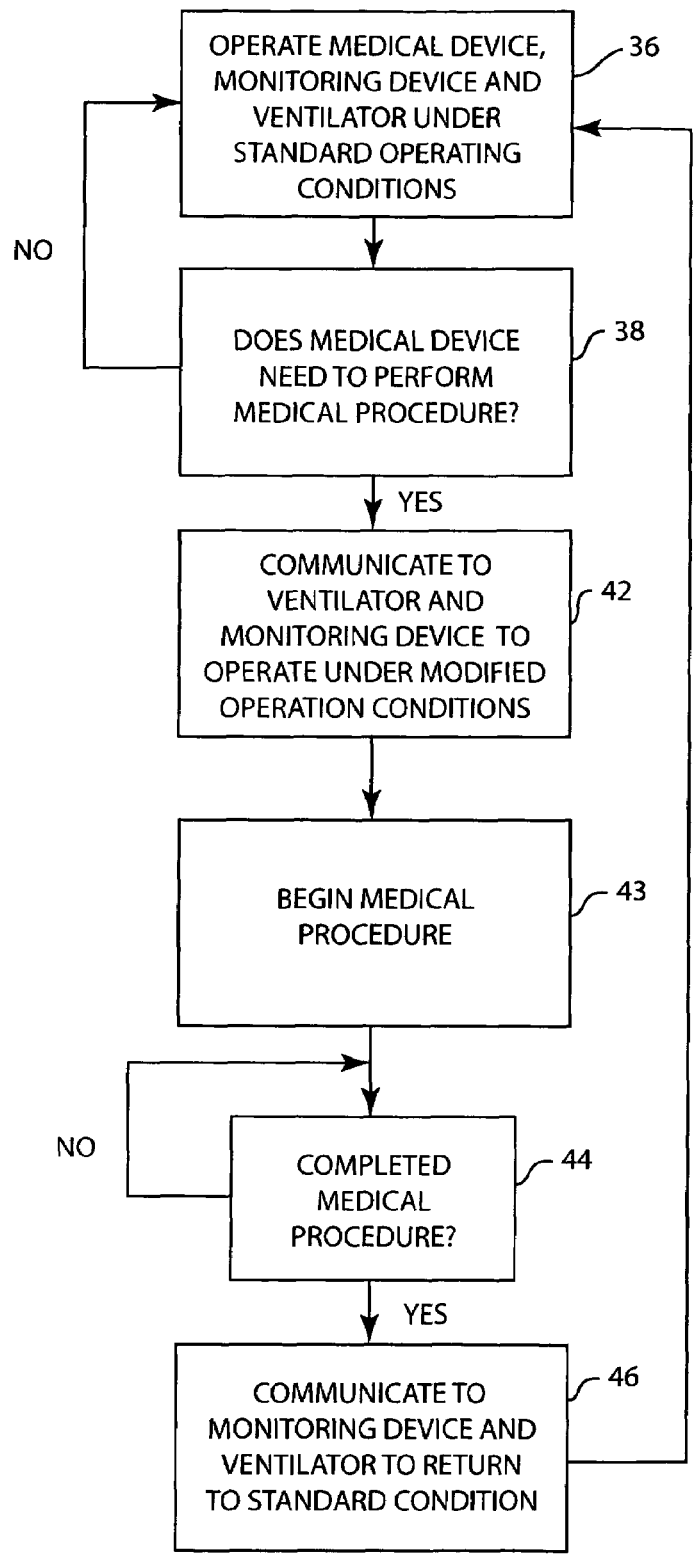
FIG. 4 is a schematic depiction of the steps of a method wherein the function of the ventilator is changed based upon the initiation of a medical procedure by a medical device.

Referring now to FIG. 4, in an alternate method of the present invention, the ventilator, monitoring device and medical device are operated under normal operating conditions, as shown in step 48. In step 50, the control unit of the ventilator is notified whether the medical device needs to carry out a medical procedure or whether the monitoring device needs to carry out a monitoring procedure. If the medical/monitoring device is not issuing a signal indicating the beginning of a medical/monitoring procedure, the system continues to operate under normal conditions. For purposes of clarity, FIG. 4 illustrates the initiation of a medical procedure with the understanding that the initiation of a monitoring procedure would be similar to the illustration of FIG. 4

Typically, the medical procedure is initiated by a user by depressing a button or display panel on the medical device. Once a user has depressed the required activation member, the medical device generates a signal to the ventilator control unit indicating that the medical device is about to begin a medical procedure. In this manner, the activation of a medical procedure at a remote medical device is communicated to the remote control unit of the ventilator.

If the ventilator control unit determines in step 50 that medical device needs to begin a medical procedure, the control unit generates a modification signal to the monitoring device to modify the normal operating condition of the monitoring device. Additionally, the control unit modifies the operation of the ventilator accordingly, as shown in step 52.

As an example of such a medical procedure, the medical device can be an imaging device such as an MRI, CT scanner or radiogram device that may be permanently or transiently integrated with a respiratory station. As a specific example, at start of a lung radiogram snapshot, the radiogram device will indicate to the control unit within the ventilator that the radiogram needs to begin a medical procedure. When taking a lung radiogram snapshot, it is desirable that the lungs of the patient be inflated to a particular pressure. Thus, when the control unit of the ventilator receives the signal from the medical device, the control unit synchronizes the operation of the ventilator with the snapshots from the lung radiogram medical device such that the snapshots can be made automatically over the course of several breaths, with the ventilator sending synchronized trigger events back to the radiogram device in conjunction with the correct moment in time for the images to be captured. Specifically, upon receiving the signal from the radiogram, the control unit of the ventilator would begin a defined procedure that consists of generating a breath with an extended inspiratory hold period, then signal the radiogram device to capture an image prior to releasing the exhalation. The medical imaging procedure would be initiated at the user interface of the radiogram device or by the ventilator's user interface. The combined ventilation therapy procedure and image capture could be set to automatically recur on a periodic basis as well. In this manner, a series of periodically timed image snapshots could be made via a single user input at the radiogram. Similar behaviors could also be applied to MRI, CT, x-ray and other imaging devices. As can be clearly understood by the above description, the improvement of the method of the present invention eliminates the user having to manually synchronize two medical devices to properly make a measurement or image and then subsequently return each device to its original, ongoing settings as it nears the completion of the procedure.

In addition to utilizing the method with imaging devices, the medical devices could also be used for drug delivery. As an example, drug delivery devices could include INO gas delivery modules, nebulizers and metered dose inhalers (MDI's).

When these drug delivery devices are used, it may be desirable to initiate a respiratory therapy procedure or, alternatively, modify the action of the devices based upon a respiratory therapy procedure. When a drug delivery device is in operative communication with the ventilator control unit, it will be possible to control the operation of the ventilator in conjunction with the activation of the drug delivery. The modified ventilator operating conditions may be to improve the deposition of drug into the lungs and may vary based upon the type of drugs being delivered.

As an example, if the medical procedure requires the aerosolized delivery of medication from the nebulizer, the control unit of the ventilator sends a modification signal to the control unit of the gas monitoring device, causing the gas monitoring device to suspend operation of the respiratory gas pump during the period of nebulization. Additionally, if other medical devices are coupled to the ventilator and may be affected by the operation of the nebulizer, the ventilator control unit provides the required signal to the medical device causing the medical device to operate under modified conditions. It should be understood that the combined respiratory therapy procedure (combination of nebulization procedure and gas monitoring device operational modification) can be initiated either at the ventilator in accordance with FIG. 3 or at the nebulization device in accordance with FIG. 4.

Contrary to the present method, known methods of using ventilator, nebulizer and monitoring devices required the user to first stop the gas monitoring, typically disconnecting the gas attachment to the breathing circuit in order to do so, and then independently initiate the nebulization procedure on the ventilator. After the procedure is completed (sometimes after 10-30 minutes) the user then needs to remember to return to the room and reinitiate gas monitoring. With doses of drugs occurring several times per day, this can become a time consuming and tedious operation.

As another specific example, for low lung infections, it may be desirable to synchronize the delivery of an antibiotic with a leading edge of a larger inspiration than had been occurring under steady state conditions. This change in the steady state would allow the antibiotic to be pushed deeper into the lungs in a more optimized fashion than would normally occur. In accordance with the invention, the drug delivery could be initiated on the drug delivery device or the ventilator. Once the initiation signal was received, the ventilator control unit would command the ventilator to perform an optimized breath and would modify (e.g. turn on) the drug delivery device for the transient period without any other user input. After the drug delivery, the ventilator and drug delivery device would return to their normal, original operating condition. Thus, in some cases, the entire procedure could be completed in a single breath.

Referring back to FIG. 4, once the operation of the ventilator and gas monitoring device have been adjusted, the medical device, such as an imaging device or drug delivery device, begins operation in step 54. As illustrated in FIG. 4, once the medical procedure has been completed, the medical device generates a signal to the control unit of the ventilator indicating that the medical procedure has been completed. Upon receiving the completed signal from the medical device, the control unit within the ventilator returns the ventilator to its normal operating condition. At the same time, the control unit returns the gas measurement device and other medical devices to their normal operating conditions. Thus, the control unit is able to affect the operation of the gas monitoring device and the ventilation operation during the medical procedure without any additional inputs from the user.

In the embodiments of the invention described, the control unit for communicating to the gas measurement device and the various other medical devices is included within the ventilator 24, as shown in FIG. 2. However, it is contemplated that the control unit could be removed from the ventilator 24, but yet be in operative communication with the ventilator 24. In any event, the control unit is in communication with at least two of the ventilator, nebulizer 18, gas measurement device 20, imaging device 22 and other medical devices 26. In this manner, the single control unit can have controlling communication with the various components to optimize not only the operation of the components but the operation of the ventilator 24 itself.

Contrary to the present method, with known prior art devices/methods, the user must often attempt to time the depression of the measurement sample key on the monitoring device with the on-going ventilation cycle. Alternatively, the user must make a number of ventilation setting changes to effect the desired ventilation therapy behavior, take the measurement using the monitoring device, then reverse the ventilation setting changes.

While this invention is susceptible to embodiments in many different forms, the drawings and specification describe in detail a preferred embodiment of the invention. They are not intended to limit the broad aspects of the invention to the embodiment illustrated.

We claim:

1. A method of integrating the operation of a ventilator and a monitoring device to perform a respiratory therapy procedure, method comprising the steps of:
    providing a first control unit integrated into the ventilator and in communication with a second control unit of the monitoring device, wherein the second control unit is remotely located from the ventilator;
    detecting the activation of a respiratory therapy procedure at the first control unit; and
    generating a modification signal from the first control unit to the second control unit to automatically modify an operating condition of the monitoring device and an operating condition of the ventilator in response to detection of the activation of the respiratory therapy procedure.

2. The method of claim 1 wherein the operating condition of the monitoring device is modified upon receipt of the modification signal.

3. The method of claim 1 further comprising the steps of:
    detecting the cessation of the respiratory therapy procedure; and
    automatically modifying the operating conditions of the monitoring device and the ventilator in response to the cessation of the respiratory therapy procedure.

4. The method of claim 3 wherein the step of automatically modifying the operating conditions of the monitoring device and the ventilator upon cessation of the respiratory therapy procedure includes returning the monitoring device and the ventilator to the operating conditions prior to activation of the next respiratory therapy procedure.

5. The method of claim 1 wherein the step of detecting the activation of the respiratory therapy procedure includes detecting an activation signal from the monitoring device that the monitoring device has initiated a monitoring procedure.

6. A method of integrating the operation of a ventilator, a monitoring device including a second control unit and a medical device to perform a respiratory therapy procedure, the method comprising the steps of:
    providing a control unit in communication with the ventilator, the monitoring device and the medical device;
    detecting either an activation signal from the monitoring device indicating that the monitoring device has initiated a monitoring procedure or an activation signal from the medical device indicating that the medical device has initiated a medical procedure; and
    generating a modification signal from the control unit to the second control unit to automatically modify an operating condition of the medical device and an operating condition of the monitoring device in response to the activation of the respiratory therapy procedure wherein the second control unit is located remote from the control unit.

7. The method of claim 6 wherein the medical device is a nebulizer and the respiratory therapy procedure includes the activation of the nebulizer to deliver an aerosolized drug into a flow of ventilation gas from the ventilator, wherein the operating condition of the monitoring device is modified to prevent the intake of the ventilation gas during the respiratory therapy procedure.

8. The method of claim 7 wherein the operation of the nebulizer begins after the modification to the operating condition of the monitoring device.

9. The method of claim 8 wherein the control unit generates a second modification signal upon termination of the respiratory therapy procedure, wherein the monitoring device and the nebulizer return to their initial operating conditions upon receipt of the second modification signal.

10. The method of claim 6 wherein the operating conditions of the medical device and the monitoring device are modified upon receipt of the modification signal.

11. The method of claim 6 wherein the control unit is integrated into the ventilator.

12. The method of claim 11 wherein the medical device includes a control unit, the medical device control unit being integrated into the ventilator.

13. The method of claim 11 wherein the medical device includes a control unit remotely located from the ventilator, wherein the ventilator control unit communicates to the medical device control unit over a communication link.

14. The method of claim 6 wherein the medical device is an imaging device.

15. The method of claim 6 wherein the medical device is a drug delivery device.

16. The method of claim 15 wherein the operating condition of the drug delivery device is modified such that the drug delivery device operation is synchronized with the operation of the ventilator to more effectively deliver the drug.

17. The method of claim 6 wherein the method includes the step of automatically modifying an operating condition of the medical device in response to the cessation of the respiratory therapy procedure.

18. A method of integrating the operation of a ventilator and a medical device, the method comprising the steps of:
providing a first control unit integrated into the ventilator and in communication with a second control unit of the medical device, wherein the second control unit is remotely located from the first control unit of the ventilator;
detecting the activation of a medical procedure at the first control unit; and
generating a modification signal from the first control unit to the second control unit to automatically modify an operating condition of the ventilator and an operating condition of the medical device in response to the activation of the medical procedure.

19. The method of claim 18 further comprising the steps of:
detecting the cessation of the medical procedure at the first control unit; and
automatically modifying the operating condition of the ventilator in response to the cessation of the medical procedure.

20. The method of claim 18 wherein the step of detecting the activation of the medical procedure includes detecting an activation signal from the medical device that the medical device has initiated the medical procedure.

21. The method of claim 18 wherein the medical device is an imaging device, wherein the activation of the medical procedure is initiated at the imaging device.

22. The method of claim 21 wherein upon initiation of the medical procedure, the operating condition of the ventilator is adjusted to optimize the medical procedure.

23. The method of claim 18 wherein the medical device is a drug delivery device.

24. The method of claim 23 wherein the activation of the medical procedure is initiated at the drug delivery device.

25. The method of claim 24 wherein upon initiation of the medical procedure, the operating conditions of the ventilator are modified to optimize the performance of the medical procedure.

26. The method of claim 23 wherein the operating condition of the drug delivery device is modified such that the drug delivery device operation is synchronized with the operation of the ventilator to more effectively deliver the drug.

27. A control system for automatically integrating the operation of a ventilator and a medical device, the system comprising:
a control unit in communication with ventilator and operable to modify the operation of the ventilator and modify the operation of the medical device via a second control unit located remotely from the control unit; and
a communication link between the control unit and the medical device such that the control unit can communicate with the medical device through the communication link,
wherein the control unit modifies the operation of the ventilator and the operation of the medical device via the second control unit in response to the activation of a respiratory therapy procedure by either the ventilator or the medical device.

28. The system of claim 27 wherein the medical device is an imaging system.

29. The control system of claim 27 wherein the communication link is a RS-422 connection.

30. The control system of claim 27 wherein the medical device is a nebulizer.

31. A control system for automatically integrating the operation of a ventilator, a medical device including a second control unit and a monitoring device to perform a respiratory therapy procedure, the system comprising:
a control unit in communication with the ventilator, the medical device and the monitoring device and operable to modify the operation of the ventilator, medical device and the monitoring device;
wherein the control unit modifies the operation of the monitoring device and the operation of the medical device via the second control unit upon activation of a respiratory therapy procedure by any of the ventilator, the medical device and the second control unit is located remotely from the control unit or the monitoring device.

32. The control system of claim 31 wherein the medical device is a nebulizer and the respiratory therapy procedure includes the activation of the nebulizer to entrain an aerosol aerolized drug into the flow of ventilation gas in the ventilator, wherein the operating condition of the monitoring device is modified to prevent the intake of the ventilation gas during the respiratory therapy procedure.

33. The control system of claim 32 wherein the nebulizer is integrated into the ventilator.

34. A control system for automatically integrating the operation of a ventilator, a medical device including a second control unit and a monitoring device to perform a respiratory therapy procedure, the system comprising:
a control unit in communication with the ventilator and operable to modify the operation of the ventilator, the medical device and the monitoring device;
a communication link between the control unit and the second control unit of the monitoring device such that the control unit can communicate with the monitoring device through the communication link; and
a communication link between the control unit and the medical device such that the control unit can communicate with the medical device through the communication link,
wherein the control unit modifies the operation at least two of the monitoring device, the medical device and the ventilator upon activation of a respiratory therapy procedure by any of the ventilator, the medical device or the monitoring device and the second control unit is located remotely from the first control unit.

35. The control system of claim 34 wherein the medical device is a nebulizer and the wherein the monitoring device is a gas monitoring device.

36. The control system of claim 34 wherein the medical device is an imaging device.

37. A control system for automatically integrating the operation of a ventilator and a monitoring device, the system comprising:
a control unit in communication with ventilator and operable to modify the operation of the ventilator and modify the operation of the monitoring device via a second control unit located remotely from the control unit; and
a communication link between the control unit and the monitoring device such that the control unit can communicate with the monitoring device through the communication link,
wherein the control unit modifies the operation of the ventilator and the operation of the monitoring device via the second control unit in response to activation of a respiratory therapy procedure.

38. The system of claim 37 wherein the monitoring device is a gas monitoring device.

* * * * *